United States Patent

Guillaume et al.

[11] Patent Number: 4,737,505
[45] Date of Patent: Apr. 12, 1988

[54] ANALGESIC 4-SUBSTITUTED INDOLES

[75] Inventors: Jacques Guillaume, Le Pre-Saint-Gervais; François Clemence, Paris; Lucien Nedelec, Le Raincy; Francoise DeLevallee, Fontenay-Sous-Bois, all of France

[73] Assignee: Roussel Uclaf, France

[21] Appl. No.: 757,515

[22] Filed: Jul. 19, 1985

[30] Foreign Application Priority Data

Jul. 19, 1984 [FR] France .................. 84 11432

[51] Int. Cl.[4] .................. A61K 31/445; C07D 401/04
[52] U.S. Cl. .................. 514/323; 514/339; 546/201; 546/273
[58] Field of Search ............... 546/273, 201; 514/323, 514/339

[56] References Cited

U.S. PATENT DOCUMENTS 4,435,408 3/1984 Nedelec et al. .................. 546/273

Primary Examiner—Jane T. Fan
Attorney, Agent, or Firm—Bierman & Muserlian

[57] ABSTRACT

Novel indole of the formula

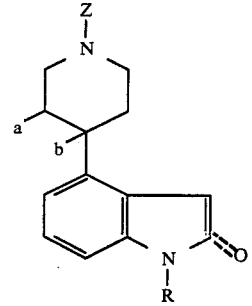

wherein R is selected from the group consisting of hydrogen, alkyl of 1 to 8 carbon atoms and aralkyl of 7 to 12 carbon atoms, Z is selected from the group consisting of hydrogen, alkyl of 1 to 8 carbon atoms, alkenyl of 2 to 8 carbon atoms, cyanoalkyl of 3 to 8 carbon atoms, hydroxyalkyl of 2 to 8 carbon atoms, $-(CH_2)_n-O-B$,

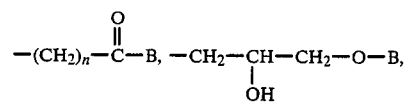

aralkyl of 7 to 12 carbon atoms optionally substituted with at least one member of the group consisting of alkyl and alkoxy of 1 to 5 carbon atoms, halogen, —OH, $CF_3-$, $CF_3O-$, $-NH_2$ and $-NO_2$ and cycloalkyl alkyl of 4 to 12 carbon atoms, n is one integer from 2 to 8, B is selected from the group consisting of aryl and heteroaryl, both optionally substituted with at least one member of the group consisting of alkyl and alkoxy of 1 to 5 carbon atoms, halogen, —OH, hydroxyalkyl of 1 to 5 carbon atoms, nitro, amino, $CF_3-$, alkenyl and alkenyloxy of 2 to 5 carbon atoms and alkynyl and alkynyloxy of 2 to 5 carbon atoms, a and b are both hydrogen or a is hydrogen and b is —OH or alkoxy of 1 to 8 carbon atoms or a and b together form a carbon-carbon bond and the 2-oxo with dotted lines indicates its possible presence with the double bond in the indole ring missing and its non-toxic, pharmaceutically acceptable acid addition salts having analgesic activity of the morphine type.

24 Claims, No Drawings

ANALGESIC 4-SUBSTITUTED INDOLES

STATE OF THE ART

Commonly assigned U.S. Pat. Nos. 4,332,808, 4,447,438 and 4,435,408 and U.S. patent application Ser. No. 535,863 filed Sept. 29, 1983 as well as French Patent No. 2,530,246 describe indole compounds similar to the compounds of Formula I but their pharmacological properties are different.

OBJECTS OF THE INVENTION

It is an object of the invention to provide the novel products of Formula I and their non-toxic, pharmaceutically acceptable acid addition salts and a process for their preparation.

It is another object of the invention to provide novel analgesic compositions and a novel method of relieving pain in warm-blooded animals.

These and other objects and advantages of the invention will become obvious from the following detailed description.

THE INVENTION

The novel indole components of the invention are selected from the group consisting of compounds of the formula

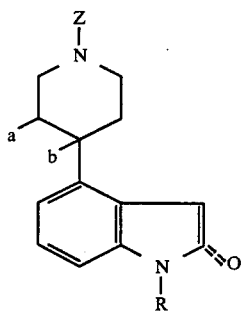

I wherein R is selected from the group consisting of hydrogen, alkyl of 1 to 8 carbon atoms and aralkyl of 7 to 12 carbon atoms, Z is selected from the group consisting of hydrogen, alkyl of 1 to 8 carbon atoms, alkenyl of 2 to 8 carbon atoms, cyanoalkyl of 3 to 8 carbon atoms, hydroxyalkyl of 2 to 8 carbon atoms, —(CH$_2$)$_n$—O—B,

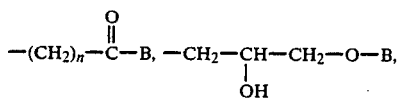

aralkyl of 7 to 12 carbon atoms optionally substituted with at least one member of the group consisting of alkyl and alkoxy of 1 to 5 carbon atoms, halogen, —OH, CF$_3$—, CF$_3$O—, —NH$_2$ and —NO$_2$ and cycloalkyl alkyl of 4 to 12 carbon atoms, n is one integer from 2 to 8, B is selected from the group consisting of aryl and heteroaryl, both optionally substituted with at least one member of the group consisting of alkyl and alkoxy of 1 to 5 carbon atoms, halogen, —OH, hydroxyalkyl of 1 to 5 carbon atoms, nitro, amino, CF$_3$—, alkenyl and alkenyloxy of 2 to 5 carbon atoms and alkynyl and alkynyloxy of 2 to 5 carbon atoms, a and b are both hydrogen or a is hydrogen and b is —OH or alkoxy of 1 to 8 carbon atoms or a and b together form a carbon-carbon bond and the 2-oxo with dotted lines indicates its possible presence with the double bond in the indole ring missing and its non-toxic, pharmaceutically acceptable acid addition salts.

Examples of R are alkyl such as methyl, ethyl, propyl, isopropyl, n-butyl, isobutyl and n-pentyl and aralkyl such as benzyl or phenethyl.

Examples of Z are alkyl such as methyl, ethyl, n-propyl, isopropyl, n-butyl, isobutyl, or n-pentyl; hydroxyalkyl such as hydroxymethyl, hydroxyethyl, hydroxypropyl, hydroxyisobutyl, hydroxyisopropyl and hydroxy-n-pentyl; cyanoalkyl such as cyanoethyl, cyanopropyl, cyanoisopropyl, cyano-n-butyl, cyanoisobutyl and cyano-n-pentyl; aralkyl such as benzyl, phenethyl or phenylpropyl optionally substituted with a halogen such as chlorine or bromine, alkyl such as methyl or ethyl and/or alkoxy such as methoxy or ethoxy; and cycloalkylalkyl such as cyclopropylalkyl or cyclohexylalkyl like cyclopropylmethyl, cyclopropylethyl, cyclopropyl-n-propyl, cyclohexylmethyl, cyclohexylethyl or cyclohexyl-n-propyl.

When Z is —(CH$_2$)$_n$—O—B,

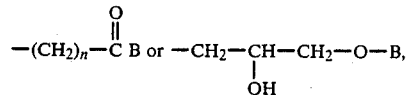

n is preferably an integer from 2 to 4 and B is aryl or heteroaryl of 4 to 12 carbon atoms such as phenyl, naphthyl, pyridyl, thienyl and thiazolyl, all optionally substituted with at least one member of the group consisting of halogen such as chlorine, bromine or fluorine, alkyl, alkoxy or hydroxyalkyl as defined above for R and Z, alkenyl such as ethenyl or propenyl, alkenyloxy such as ethenyloxy or propenyloxy, alkynyl such as ethynyl or propynyl and alkynyloxy such as propynyloxy. When b is alkoxy, it is preferably methoxy or ethoxy.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, propionic acid, formic acid, benzoic acid, maleic acid, fumaric acid, succinic acid, tartaric acid, citric acid, oxalic acid, glyoxylic acid, aspartic acid and alkanesulfonic acids such as methane sulfonic acid and arylsulfonic acids such as benzene sulfonic acid.

Among the preferred compounds of Formula I are those wherein R is hydrogen or alkyl of 1 to 4 carbons atoms, those wherein Z is hydrogen or alkyl of 1 to 4 carbon atoms, those wherein Z is —(CH$_2$)$_n$—O—B or

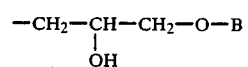

and n is 2 to 4 and B is optionally substituted phenyl or thienyl, those wherein a and b are both hydrogen, those where a and b together form a carbon-carbon bond; those wherein a is hydrogen and b is methoxy or —OH and their non-toxic, pharmaceutically acceptable acid addition salts.

More preferred are the compounds of Formula I wherein Z is

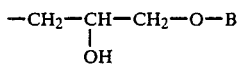

and B is phenyl substituted with propenyloxy and their non-toxic, pharmaceutically acceptable acid addition salts.

Examples of specific preferred compounds of Formula I are 1,3-dihydro-4-[1-(2-hydroxy-3-[2-(2-propenyloxy)-phenoxy]-propyl]-1,2,3,6-tetrahydro-4-pyridinyl]-2H-indole-2-one and its hydrochloride, 4-(4-methoxy-4-piperidinyl)-1H-indole and its fumarate and 4-(1H-indol-4-yl)α-[[2-(2-propenyloxy)-phenoxy]-methyl]-1,2,3,6-tetrahydro-1-pyridine-ethanol and its oxalate.

The novel process of the invention for the preparation of a compound of Formula I comprises condensing N-benzyl-4-piperidone with a compound of the formula

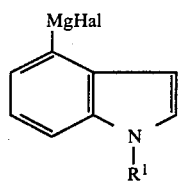

II wherein Hal is a hydrogen and $R^1$ is alkyl of 1 to 8 carbon atoms or aralkyl of 7 to 12 carbon atoms to obtain a compound of the formula

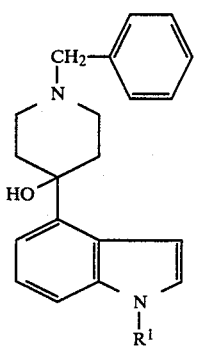

$I_A$ optionally reacting the latter compound with an agent for cleaving the benzyl group on the piperidinyl nitrogen to form a compound of the formula

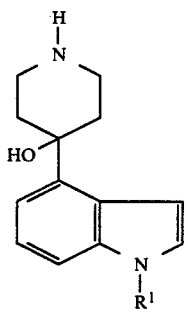

$I_B$ optionally subjecting the latter to a dehydration agent to form a compound of the formula

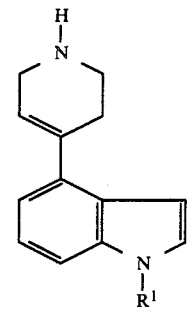

$I_C$ or wherein $R^1$ is benzyl, optionally reacting the compound of Formula $I_A$ with a selective cleavage agent to remove the benzyl from the indole to obtain a compound of the formula

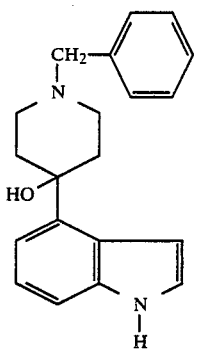

$I_D$ optionally subjecting the latter to an agent to cleave the benzyl from the piperidinyl nitrogen to form a compound of the formula

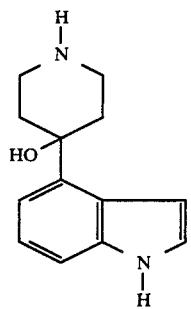

$I_F$

When any of the above compounds of Formula I has Z as hydrogen, the compound may be reacted with an agent capable of introducing $Z^1$ when $Z^1$ is Z other than hydrogen to obtain the corresponding compound of Formula I with $Z^1$ on the piperidinyl nitrogen and optionally subjecting the compounds of Formula I when Z is $Z^1$ and R is hydrogen to an alkylation or aralkylation agent to obtain the compound of Formula I wherein R is alkyl of 1 to 8 carbon atoms or aralkyl of 7 to 12 carbon atoms.

When one of the compounds of Formula I has b as hydroxyl, it may be reacted with an etherification agent to obtain a compound of Formula I wherein b is alkoxy of 1 to 8 carbon atoms or reacted with a dehydration agent to obtain a compound of Formula I wherein a and b form a carbon-carbon bond and the latter may optionally be reacted with a reducing agent to form a compound of Formula I wherein a and b are hydrogen or reacted with a cleavage agent for —OH to obtain a compound of Formula I wherein a and b are hydrogen.

The above compounds of Formula I may also be reacted with a halogenation agent to introduce a halogen at the 3-position of the indole ring and the latter may be hydrolyzed to form a compound of Formula I having a 2-oxo group. Another compound of Formula I may be reacted with an approximately stoichiometric amount of an acid in an alkanol or mixtures thereof or a mixture of an alkanol and ethyl acetate to form the acid addition salt thereof.

In a preferred embodiment of the process of the invention. $Z^1$ is introduced by hydroxymethylation followed by reduction of the methylol group when $Z^1$ is methyl or with a compound of the formula $Z^1$-Hal where Hal is a halogen and $Z^1$ is alkyl of 1 to 8 carbon atoms, alkenyl of 2 to 8 carbon atoms, hydroxyalkyl of 2 to 8 carbon atoms, cyanoalkyl of 3 to 8 carbon atoms, aralkyl of 7 to 12 carbon atoms, cycloalkylalkyl of 4 to 12 carbon atoms, $-(CH_2)_n-O-B$ or

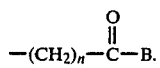

When $Z^1$ is

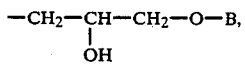

$Z^1$ is introduced by reaction with an epoxide of the formula

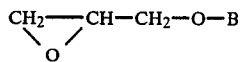

and when $Z^1$ is $CN-CH_2-CH_2-$, $Z^1$ is introduced by reaction with acrylonitrile.

In a preferred embodiment of the process, Hal in Formula II is chlorine or bromine and when a and b are not a carbon-carbon bond, the benzyl is removed from the piperidinyl nitrogen with hydrogen in the presence of a catalyst such as palladium. The dehydration agent is a strong acid such as hydrochloric acid or oxalic acid or phosphoric acid anhydride and the cleavage agent to remove the benzyl from the indole ring is sodium in ammonia at low temperatures.

To form the compounds of Formula I when R is alkyl or aralkyl, a compound of Formula I wherein R is hydrogen is reacted with an alkyl halide or aralkyl halide such as the chloride, bromide or iodide in the presence of a base such as potassium hydroxide in dimethyl sulfoxide or preferably sodium hydride in the presence of dimethylformamide. To form compounds of Formula I where b is alkoxy, a compound of Formula I wherein b is hydroxyl is reacted with an etherification agent such as an alcohol in an anhydrous acid medium To obtain compounds of Formula I where a and b are both hydrogen, either a compound of Formula I when b is hydroxyl is reacted with lithium in liquid amonia at $-35°$ to $-60°$ C. or a compound of Formula I wherein a and b form a carbon-carbon bond is reacted with hydrogen in the presence of a catalyst such as palladium.

To form the compounds of Formula I with a 2-oxo group, the hydrogen is introduced at the 3-position of the indole ring by reaction with a N-halo- sucoinimide such as N-chloro succinimide or N-bromosuccinimide and hydrolysis of the 3-halo compound may be effected with an acid such as hydrochloric acid When $Z^1$ is methyl, the hydroxymethylation is effected with formaldehyde in methanol and the reduction is effected with sodium tetrahydroboride. When $Z^1$-Hal is used, Hal is chlorine, bromine or iodine When $Z^1$ is hydroxyalkyl, the hydroxyl is protected in the form of a pyran derivative which can be removed by reaction with an acid such as hydrochloric acid or sulfuric acid. When Z is

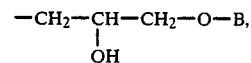

the epoxide is reacted in an alkanol, such as methanol or ethanol, at reflux.

The novel analgesic compositions of the invention are comprised of an analgesically effective amount of at least one compound of Formula I and its non-toxic, pharmaceutically acceptable acid addition salts and an inert pharmaceutical carrier or excipient. The compositions may be in the form of tablets, dragees, capsules, granules, suppositories, injectable solutions or suspensions, ointments, creams, gels and aerosol preparations.

Examples of suitable excipients are talc, gum arabic, lactose, starch, magnesium stearate, cocoa butter, aqueous and non-aqueous vehicles, animal or vegetable fatty bodies, paraffin derivatives, glycols, various wetting agents, dispersants and emulsifiers and preservatives.

The compositions have a strong affinity for opiate receptors, especially for $\mu$ receptors and have analgesic properties of the morphine type. Some compounds of Formula I also have an affinity for K receptors. The compositions are useful for treatment of intense pain, especially pain resistant to peripheral antalgics such as during neoplastic processes, in the treatment of pancreatitis, nephritic or biliary colic and in the treatment of post-operative and post-traumatic pain.

Among the preferred compositions of the invention are those where the active ingredient is selected from the group consisting of 1,3-dihydro-4-[1-(2-hydroxy-3-[2-(2-propenyloxy)-phenoxy]-propyl)-1,2,3,6-tetrahydro-4-pyridinyl]-2H-indole-2-one and its hydrochloride, 4-(4-methoxy-4-piperidinyl)-1H-indole and its fumarate and 4-(1H-indole-4-yl-α-[[2-(2-propenyloxy)-phenoxy]-methyl]-1,2,3,6-tetrahydro-1-pyridine-ethanol and its oxalate.

The novel method of the invention for relieving pain in warm-blooded animals, including humans, comprises administering to warm-blooded animals an analgesically effective amount of at least one compound of Formula I and its non-toxic, pharmaceutically acceptable acid addition salts. The compounds may be administered orally, rectally, parenterally or topically to the skin and mucosa. The usual daily dose is depending on the specific compound, method of administration and condition treated. The usual parenteral daily dose is 0,07 to 0,7 mg/kg, for the adult.

The starting compounds of Formula II may be prepared as described in French Patent No. 2,458,549 and as described in the following examples.

In the following examples, there are described several preferred embodiments to illustrate the invention. However, it should be understood that the invention is not intended to be limited to the specific embodiments.

EXAMPLE 1

1-benzyl-4-[1-benzyl-1H-indol-4-yl]-4-piperidinol hydrochloride 9 g of magnesium and 24.2 g of N-benzyl-4-chloro-indole were reacted as in stage A of Example 1 of French Patent No. 2,458,549 to form the magnesium derivative of N-benzyl-4-chloro-indol. A solution of 17.7 g of N-benzyl-4-piperidinone in 40 ml of tetrahydrofuran were introduced into the acid solution at 30° C. while keeping the temperature below 40° C. The mixture was refluxed for 2 hours and then was cooled to 10° C. after which an aqueous saturated ammonium chloride solution was added thereto. The mixture was filtered to remove excess magnesium and the filtrate was extracted with ethyl acetate. The organic phase was washed with aqueous sodium hydroxide, was dried and evaporated to dryness under reduced pressure. The 42 g of brown oil residue were dissolved in 400 ml of ethyl acetate and a saturated solution of hydrogen chloride in ethyl acetate was added thereto. The mixture was filtered and the product was dried under reduced pressure and crystallized from an isopropanol-methanol mixture to obtain 17.3 g of 1-benzyl-4-[1-benzyl-1H-indole-4-yl]-4-piperidinol hydrochloride with a melting point of 270° C. The free base was obtained by treatment of the salt with sodium hydroxide, extraction with ethyl acetate and evaporation of the organic phase.

EXAMPLE 2

1-benzyl-4-[1H-indol-4-yl]-4-piperidinol hydrochloride

A solution of 6.5 g of the free base of Example 1 in 250 ml of tetrahydrofuran was added with stirring at −40° C. under nitrogen to 500 ml of liquid ammonia and then 4 g of pieces of sodium were slowly added at −40° C. The mixture was stirred at −40° C. for 30 minutes and was decolorized by addition of ammonium chloride. The ammonia was evaporated and the mixture was taken up in water. The aqueous phase was extracted with ethyl acetate and the organic phase was washed with water, dried and evaporated to dryness under reduced pressure. The residue was chromatographed over silica gel and was eluted with a 6-3-1 cyclohexane-chloroform-triethylamine mixture. The product was triturated in cyclohexane, was filtered and dried to obtain 12.2 g of the free base melting at 108° C. The latter was dissolved in ethyl acetate and saturated hydrogen chloride in solution in ethyl acetate was added thereto to obtain 13.7 g of 1-benzyl-4-[1H-indol-4-yl]-4-piperidinol hydrochloride melting at 200° C.

EXAMPLE 3

4-(1H-indol-4-yl)-4-piperidinol hydrochloride

A mixture of 13.7 g of the hydrochloride of Example 2 in 600 ml of methanol was subjected to hydrogen at 40° C. in the presence of 4.7 g of palladized charcoal and the mixture was then filtered. The filtrate was evaporated to dryness under reduced pressure at 40° C. and the residue was triturated in ether, filtered and dried at 20° to 25° C. under reduced pressure to obtain 7.9 g of 4-(1H-indol-4-yl)-4-piperidinol hydrochloride melting at 270° C.

The said salt was treated with aqueous sodium hydroxide and the solution was extracted with ethyl acetate to obtain the corresponding free base.

EXAMPLE 4

4-(1H-indol-4-yl)-1-methyl-4-piperidinol fumarate 2.5 ml of a 37% aqueous solution of formic aldehyde were slowly added at 8° to 10° C. to a solution of 5 g of the base of Example 3 in 50 ml of methanol and the mixture was stirred at 5° to 10° C. for 15 minutes during which crystallization occurred. 100 ml of methanol were added thereto and after the temperature returned to room temperature, the mixture was stirred until dissolution.

The solution was cooled to 5° to 8° C. and then 2.62 g of 95% sodium borohydride were added thereto while holding the temperature below 11° C. The temperature rose to room temperature and the mixture was stirred for one hour and poured into 300 ml of water. The mixture was filtered and the product was washed with water and dried at 70° C. to obtain 4.45 g of product. The filtrate was made alkaline by addition of potassium carbonate and was extracted with ethyl acetate. The organic phase was washed with aqueous sodium chloride solution, dried and evaporated to dryness to obtain 1.27 g of oil residue. The combined residue and product were dissolved in acetone and chromatographed over silica gel. Elution with a 6-3-1 chloroform-acetone-triethylamine mixture yielded 2.8 g of 4-(1H-indol-4-yl)-1-methyl-4-piperidinol melting at 205°–206° C.

The said product was dissolved in 280 ml of isopropanol and a solution of 1.41 g of fumaric acid in isopropanol was added thereto. The mixture was refluxed while isopropanol was added to effect dissolution and was then cooled for crystallization and filtered. The product was rinsed with isopropanol to obtain 0.730 g of neutral 4-(1H-indol-4-yl)-1-methyl-4-piperidinol fumarate melting at 240° C. The mother liquors were concentrated, cooled and filtered. The product was rinsed with isopropanol and dried under reduced pressure at 70° C. to obtain 2.03 g of the acid fumarate melting at 210°–211° C.

EXAMPLE 5

4-(1-methyl-1,2,3,6,-tetrahydropyridin-4-yl)-1H-indole fumarate

A mixture of 6.4 g of the free base of Example 4 and 200 ml of 1N hydrochloric acid was refluxed for 90 minutes and was then cooled to room temperature and was diluted with water. The mixture was made alkaline by addition of potassium carbonate and was then extracted with ethyl acetate. The organic phase was washed with water, dried and evaporated to dryness under reduced pressure. The 5.7 g of residue were chromatographed over silica gel and eluted with a 6-3-1 cyclohexane-chloroform-ethyl acetate mixture to obtain 2.5 g of 4-(1-methyl-1,2,3,6-tetrahydropyridin-4-yl)-1H-indole melting at 164° C.

The said product was dissolved in 150 ml of isopropanol at 60° C. and 1.4 g of fumaric acid were added thereto. Solution took place and was followed by crystallization and the crystals were dissolved in 100 ml of methanol. The solution was concentrated, cooled and filtered. The product was dried under reduced pressure to obtain 3.4 g of 4-(1-methyl-1,2,3,6,-tetrahydropyridin-4-yl)-1H-indole fumarate melting at 170° C. and then at 184° C.

EXAMPLE 6

1-propyl-4-(1H-indol-4-yl)-4-piperidinol

A mixture of 6 g of the hydrochloride of Example 3, 120 ml of dimethylformamide, 7.5 g of sodium carbonate and 3 ml of propyl iodide was stirred under nitrogen and then stood at room temperature for 5 hours. The mixture was extracted with ethyl acetate and the organic phase was washed with water, dried and evaporated to dryness under reduced pressure to obtain 5.15 g of 1-propyl-4-(1H-indol-4-yl)-4-piperidinol.

EXAMPLE 7

4-(1-propyl-1,2,3,6-tetrahydropyridin-4-yl)-1H-indole fumarate

Using the procedure of Example 5, 5.15 g of the product of Example 6 were reacted to obtain 2.55 g of 4-(1-propyl-1,2,3,6-tetrahydropyridin-4-yl)-1H-indole melting at 105° C. The latter was reacted with fumaric acid as in Example 5 to obtain 3.2 g of 4-(1-propyl-1,2,3,6-tetrahydropyridin-4-yl)-1H-indole acid fumarate melting at 192° C.

EXAMPLE 8

4-(4-piperidinyl)-1H-indole

A solution of 650 mg of the hydrochloride of Example 3, 11 ml of tetrahydrofuran and 2.7 g of ethanol was added with stirring under nitrogen at −40° C. to 60 ml of liquid ammonia and 200 mg of lithium were added thereto in small amounts over one hour. The ammonia was evaporated at room temperature and the residue was taken up in water and extracted with ethyl acetate. The organic phase was washed with water, aqueous sodium chloride, was dried and filtered and evaporated to dryness under reduced pressure at 40° C. The 0.596 g of residue were chromatographed over silica gel and eluted with a 7-2-1 chloroform-methanol-triethylamine mixture to obtain 0.350 g of 4-(4-piperidinyl)-1H-indole melting at 230° C.

EXAMPLE 9

4-(1H-indol-4-yl)α-[[2-(2-propenyloxy)phenoxyl]methyl]-1-piperidine ethanol and its neutral succinate A suspension of 3.5 g of the product of Example 8, 3.95 g of 2-[2-prop-2-enyloxy)-phenoxy]-methyl oxirane (prepared as in Belgium patent no. 699,402) and 70 ml of ethanol was refluxed for two hours under nitrogen with stirring and the solvent was evaporated. The residue was chromatographed over silica gel and was eluted with a 6-3-1 cyclohexane-chloroform-triethylamine mixture to obtain 4.88 g of 4-(1H-indol-4-yl)α-[[2-(2-propenyloxy)-phenoxy]-methyl]-1-piperidine-ethanol with an Rf=0.13.

A solution of 3.25 g of the said base in 150 ml of isopropanol was admixed with 472 mg of succinic acid and the resulting solution was heated for 30 minutes and was concentrated. Crystallization was started and after standing at room temperature for 20 hours, the mixture was filtered. The crystals were dried under reduced pressure to obtain 2.8 g of 4-(1H-indol-4-yl)α-[[2-(2-propenyloxy) phenoxy ]methyl]-1-piperidine ethanol as its neutral succinate melting at 125° C.

EXAMPLE 10

4-hydroxy-4-(1H-indol-4-yl)-α-[[2-(2-propenyloxy)-phenoxy]-methyl]-1-piperidine-ethanol hydrochloride A suspension of 1 g of the free base of Example 3, 20 ml of ethanol and 900 mg of 2-[2-(prop-2-enyloxy)-phenoxy]-methyl oxirane was refluxed with stirring under nitrogen for 5 hours and the mixture was then diluted with water and made alkaline by addition of sodium hydroxide. The mixture was extracted with ethyl acetate and the organic phase was evaporated to dryness. The residue was chromatographed over silica gel and was eluted with a 8-1-1 chloroform-acetone-triethylamine mixture to obtain 710 mg of 4-hydroxy--4-(1H-indol-4-yl)-α-[[2-(2-propenyloxy)-phenoxy]-methyl-1-piperidine-ethanol with an Rf=0.25.

A saturated solution of hydrogen chloride in ethyl acetate was added to a solution of 1.6 g of the said base in 200 ml of ethyl acetate and 20 ml of methanol and crystallization was started. The mixture was concentrated, cooled and filtered and the product was dried under reduced pressure to obtain 1.6 g of 4-hydroxy-4-(1H-indol-4-yl)-α-[[2-(2-propenyloxy)-phenoxy]-methyl]1-piperidine-ethanol hydrochloride melting at 185° C.

EXAMPLE 11

Neutral oxalate of 4-(1H-indol-4-yl)-α-[[2-(2-propenyloxy)-phenoxy]-methyl]-1,2,3,6-tetrahydro-1-pyridine ethanol A solution of 9.3 g of the free base of Example 10, 300 ml of 1N hydrochloric acid and 100 ml of ethanol was refluxed for 3 hours and the mixture was diluted with water and made alkaline. The aqueous phase was saturated with potassium carbonate and was extracted with ethyl acetate. The organic phase was chromatographed over silica gel and eluted with a 6-3-1 cyclohexane-chloroform-triethylamine mixture to obtain 7.7 g of 4-(1H-indole-4-yl)-α-[[2-(2-propenyloxy)-phenoxy]-methyl]-1,2,3,6-tetrahydro-1-pyridine ethanol with an Rf=0.05.

1.2 g of oxalic acid were added to a solution of 7.7 g of the said free base in 300 ml of isopropanol and 300 ml of methanol and the mixture was refluxed for 30 minutes and was concentrated and cooled. Crystallization was induced and the mixture was filtered. The product was dried under reduced pressure to obtain 6.7 g of the neutral oxalate salt of the base melting at 163° C.

EXAMPLE 12

Acid sulfate of 4-(1-methyl-1H-indol-4-yl)-α-[[2-(2-propenyloxy)-phenoxy]-methyl]-1,2,3,6-tetrahydro-1-pyridine-ethanol A mixture of 6.1 g of the free base of Example 11, 50 ml of dimethylformamide and 725 mg of 55% sodium hydride was heated at 50° C. with stirring under nitrogen for 30 minutes and after cooling to 0° C., 1 ml of methyl iodide was added. The mixture was heated at 40° C. for 3 hours, was cooled to 10° C. and 100 ml of water were added thereto. The mixture was extracted with ethyl acetate and the organic phase was chromatographed over silica gel. Elution with a 6-3-1 cyclohexane-chloroform-triethylamine mixture yielded 3.2 g of 4-(1-methyl-1H-indol-4-yl)-α-[[2-(2-propenyloxy)- phenoxy]-methyl]-1,2,3,6-tetrahydro-1-pyridine-ethanol with an Rf=0.20.

A molar solution of sulfuric acid in isopropanol may be added to a solution of 2.9 g of the said base in 100 ml of isopropanol to obtain an acid pH and the mixture was concentrated to 50 ml, cooled and filtered. The product was dried under reduced pressure to obtain 3.1 g of acid sulfate of 4-(1-methyl-1H-indol-4-yl)- α-[[2-(2-propenyloxy)-phenoxy]-methyl]-1,2,3,6-tetrahydro-1-pyridine-ethanol melting at 150° C.

EXAMPLE 13

1,3-dihydro-4-[1-[2-hydroxy-3-[2-(2-propenyloxy)-phenoxy]propyl]-1,2,3,6-tetrahydro-4-pyridinyl]-2H-indol-2-one and its hydrochloride A solution of 6.6 g of the free base of Example 11, 80 ml of acetic acid and 2.5 g of N-chloro succinimide was stirred under nitrogen for one hour and was then diluted with water and made alkaline by addition of potassium carbonate. The mixture was extracted with ethyl acetate to obtain 8.8 g of the 3-chloro derivative which was used as is.

A mixture of 8.8 g of the 3-chloro derivative, 100 ml of ethanol and 200 ml of N hydrochloric acid was made alkaline by addition of sodium hydroxide. The aqueous phase was saturated with potassium carbonate and was extracted with ethyl acetate. The resulting 6.7 g of resin were dissolved in 200 ml of refluxing ethyl acetate and the solution was concentrated. Crystallization was induced and the mixture was cooled and filtered. The crystals were dried under reduced pressure to obtain 3.1 g of the free base melting at 130°–135° C.

A solution of 4.1 g of the said base in 400 ml of isopropanol and 200 ml of methanol was heated to reflux and cooled after which a saturated solution of hydrogen chloride in isopropanol was added to obtain an acid pH. The methanol was distilled and the isopropanol solution was concentrated, cooled and filtered. The product was dried at 80° C. under reduced pressure and the 3.9 g of product were recrystallized from a refluxing mixture of ethyl acetate and methanol. After concentration, cooling and filtering, the product was dried under reduced pressure at 80° C. to obtain 3.6 g of 1,3-dihydro-4-[1-[2-hydroxy-3-[2-(2-propenyloxy)-phenoxy]propyl]-1,2,3,6-tetrahydro-4-pyridinyl]-2H-indol-2-one hydrochloride melting at 190° C.

EXAMPLE 14

4-(4-methoxy-4-piperidinyl)-1H-indole

A mixture of 13 g of the hydrochloride of Example 3, 140 ml of methanol and 70 ml of a freshly prepared saturated solution of hydrogen chloride in methanol was stirred under nitrogen at room temperature for one hour and potassium carbonate was added thereto at 0° to 5° C. to obtain an alkaline pH. The mixture was diluted with water and was extracted with ethyl acetate. The organic phase was dried, filtered and evaporated to dryness under reduced pressure and the residue was chromomatographed over silica gel. Elution with a 6-3-1 chloroform-acetone-triethylamine mixture yielded 8.8 g of product and 3.4 g thereof were dissolved in refluxing acetone. The solution was filtered hot and the filtrate was concentrated and cooled. Crystallization was induced and the crystals were recovered by filtration and dried under reduced pressure at room temperature to obtain 2.45 g of 4-(4-methoxy-4-piperidinyl)-1H-indole melting at 216° C.

1.23 g of fumaric acid were added to a solution of 2.45 g of the said base in 200 ml of isopropanol and the mixture was refluxed for 30 minutes. The solution was concentrated, cooled and filtered and the product was dried under reduced pressure at 80° C. to obtain 3.15 g of the acid fumarate of the base melting at 220° C.

EXAMPLE 15

4-(1H-indol-4-yl)-4-methoxy-α-[[2-(2-propenyloxy-phenoxy]methyl]-1-piperidine-ethanol A mixture of 3.2 g of the free base of Example 14, 3.15 g of 2-[[2-(prop-2-enyloxy)-phenoxy]-methyl] oxirane and 100 ml of ethanol was refluxed with stirring under nitrogen for four hours and ethanol was distilled at 50° C. under reduced pressure. The residue was chromatographed over silica gel and eluted with a 6-3-1 chloroform-cyclohexane-triethylamine mixture to obtain 3.1 g of 4-(1H-indol-4-yl)-4-methoxy-α-[[2-(2- propenyloxy-phenoxy]- methyl]-1-piperidine-ethanol with an Rf=0.60.

1 g of dl tartaric acid was added to a solution of 2.95 g of the said base in isopropanol and the mixture was refluxed for 15 minutes, concentrated and cooled. The mixture was filtered and the product was dried under reduced pressure at 80° C. to obtain 2.6 g of the neutral tartrate of the free base melting at 178° C.

EXAMPLE 16

1-butyl-4-(1H-indol-4-yl)-4-piperidinole

Using the procedure of Example 6, 6.3 g of the hydrochloride of Example 3, 125 ml of dimethylformamide, 5.36 ml of 1-bromo-butane and 6.625 g of sodium carbonate were reacted to obtain after crystallization from methanol 5.33 g of 1-butyl-4-(1H-indol-4-yl)-4-piperidinole melting at≈100° C.

EXAMPLE 17

4-(1-butyl-1,2,3,6-tetrahydropyridin-4-yl)1H-indole

A solution of 5 g of the product of Example 16 in 80 ml of ethanol and 160 ml of 1N hydrochloric acid was refluxed for 3 ½ hours and was then cooled and made alkaline by addition of 2N sodium hydroxide solution. The mixture was extracted with ethyl acetate and the organic phase was washed with water, dried and evaporated to dryness under reduced pressure. The 5.3 g of residue were chromatographed over silica gel and eluted with a 6-3-1 chloroform-cyclohexane-triethylamine mixture to obtain 3.59 g of 4-(1-butyl-1,2,3,6-tetrahydropyridin-4-yl)1H-indole melting at 91° C.

685 mg of fumaric acid were added to a solution of 1.5 g of the free base in 30 ml of ethanol at room temperature and the mixture was stirred for 90 minutes and filtered. The product was rinsed with ethanol and dried under reduced pressure at 80° C. to obtain 1.51 g of the acid fumarate of the base melting at 181°–182° C.

EXAMPLE 18

1,3-dihydro-4-(1-butyl-1,2,3,6-tetrahydropyridin-4-yl)-2H-indol-2-one

Using the procedure of Example 13, 2.1 g of the free base of Example 17, 21 ml of acetic acid and 1.2 g of N-chloro-succinimide were reacted to obtain 1.75 g of the 3-chloro derivative melting at 163°–164° C.

A solution of 1.61 g of the 3-chloro derivative in 24 ml of ethanol and 24 ml of N hydrochloric acid was stirred under an inert atmosphere at room temperature for 24 hours and was then poured into water. The mixture was made alkaline by addition of sodium hydroxide solution and was extracted with ethyl acetate. The organic phase was washed with water, dried and evaporated to dryness to obtain 1.52 g of 1,3-dihydro-4-(1-butyl-1,2,3,6-tetrahydropyridin-4-yl)-2H-indol-2-one melting at 110°–111° C.

A solution of the said base in 50 ml of ethanol was acidified with a saturated solution of hydrogen chloride in ethyl acetate and after standing at 40° C. for 16 hours, the mixture was filtered. The product was rinsed with ethanol, dried under reduced pressure at 80° C. and crystallized from a methanol-ethanol mixture to obtain 0.866 g of the hydrochloride of the base melting at 266° C.

EXAMPLE 19

1-ethyl-4-(1H-indol-4-yl)-4-piperidinol

Using the procedure of Example 6, 6.3 g of the hydrochloride of Example 3, 125 ml of dimethylformamide, 2.8 ml of bromoethane and 6.625 g of potassium carbonate were reacted to obtain after ether extraction and crystallization from methanol 2.11 g of 1-ethyl-4-(1H-indol-4-yl)-4-piperidinol melting at 135° C.

EXAMPLE 20

4-(1-ethyl-1,2,3,6-tetrahydropyridin-4-yl)-1H-indole

Using the procedure of Example 17, 2 g of the product of Example 19, 34 ml of ethanol and 66 ml of N hydrochloric acid were reacted to obtain 1.28 g of 4-(1-ethyl-1,2,3,6-tetrahydropyridin-4-yl)-1H-indole melting at 151° C.

1.28 g of the said base were reacted as in Example 17 to obtain 1.504 g of the acid fumarate of the free base melting at 200° C.

EXAMPLE 21

1,3-dihydro-4-(1-ethyl-1,2,3,6-tetrahydropyridin-4-yl)-2H-indol-2-one hydrochloride Using the procedure of Example 13, 1.25 g of the free base of Example 20, 12 ml of acetic acid and 0.911 g of N-chlorosuccinimide were reacted to obtain 1.21 g of the 3-chloro derivative. A solution of the latter in 18 ml of ethanol and 18 ml of N hydrochloric acid was stirred under an inert atmosphere at room temperature for 23 hours during which total dissolution was followed by gradual crystallization. The mixture was filtered and the product was rinsed with ethanol, dried and crystallized from a methanol ethanol mixture to obtain 0.85 g of 1,3-dihydro-4-(1-ethyl-1,2,3,6-tetrahydropyridin-4-yl)-2H-indol-2-one hydrochloride melting at >280° C.

EXAMPLE 22

1,3-dihydro-4-(1-propyl-1,2,3,6-tetrahydropyridin-4-yl)-2H-indol-2-one hydrochloride Using the procedure of Example 13, 0.689 g of the base of Example 7, 7 ml of acetic acid and 0.421 g of N-chloro-succinimide were reacted to obtain 0.581 g of the 3-chloro derivative. The latter was reacted as in Example 21 to obtain 0.369 g of 1,3-dihydro-4-(1-propyl-1,2,3,6-tetrahydropyridin-4-yl)-2H-indol-2-one hydrochloride melting at ≃280° C.

EXAMPLE 23

1,3-dihydro-4-(1-propyl-piperidin-4-yl)-2H-indol-2-one hydrochloride 1.69 g of the hydrochloride of Example 22 were hydrogenated in 300 ml of ethanol in the presence of 0.8 g of 10% palladized charcoal and the mixture was filtered. The filtrate was evaporated to dryness and the product was crystallized from ethanol to obtain 1.24 g of 1,3-dihydro-4-(1-propyl-piperidin-4-yl)-2H-indol-2-one hydrochloride melting at 270°–275° C.

EXAMPLE 24

4-(1H-indol-4-yl)-1-(2-phenylethyl)-4-piperidinol

Using the procedure of Example 6, 8 g of the hydrochloride of Example 3, 100 ml of dimethylformamide, 10 g of sodium carbonate and 5.2 ml of β-phenylethyl bromide were reacted to obtain 7.8 g of 4-(1H-indol-4-yl-1-(2-phenylethyl)-4-piperidinol melting at 194° C.

0.47 g of dl tartaric acid were added to a solution of 1 g of the above base in 200 ml of isopropanol and the mixture was refluxed for 15 minutes, concentrated, cooled and filtered. The product was dried at 80° C. under reduced pressure and was crystallized from a methanol-isopropanol mixture to obtain 1.2 g of the acid tartrate of the free base melting at 245° C.

EXAMPLE 25

4-[1-(2-phenethyl)-1,2,3,6-tetrahydro-pyridin-4-yl]-1H-indole

Using the procedure of Example 17, 6.4 g of the free base of Example 24 were reacted and the 6.6 g of product was chromatographed over silica gel and eluted with a 6-3-1 cyclohexane-chloroform-triethylamine mixture to obtain 4-[1-(2-phenethyl)-1,2,3,6-tetrahydro-pyridin-4-yl]-1H-indole.

A solution of 4.5 g of the free base in 100 ml of isopropanol cooled to 0° to 5° C. was admixed with a saturated solution of hydrogen chloride in ethyl acetate to obtain an acid pH. The mixture was filtered and the product was washed with isopropanol and dried under reduced pressure at 60° C. The product was crystallized from a mixture of isopropanol and ethanol to obtain 3.35 g of the hydrochloride of the base melting at 230° C.

EXAMPLE 26

1,3-dihydro-4-[1-(2-phenylethyl)-1,2,3,6-tetrahydro-4-pyridinyl]-2H-indole-2-one hydrochloride Using the procedure of Example 13, 1.43 g of the base of Example 25, 15 ml of acetic acid and 0.7 g of N-chlorosuccinimide were reacted to obtain 1.8 g of crude product which were chromatographed over silica gel and eluted with a 6-3-1 cyclohexane-chloroform-triethylamine mixture to obtain the 3-chloro derivative.

A solution of 1 g of the said chloro derivative in 30 ml of ethanol and 20 ml of N hydrochloric acid was heated at 80° C. for one hour and was then cooled and filtered. The product was washed with ethanol and dried under reduced pressure at 80° C. to obtain 0.7 g of 1,3-dihydro-4-[1-(2-phenylethyl)-1,2,3,6-tetrahydro-4-pyridinyl]-2H-indole-2-one hydrochloride melting at 270° C.

EXAMPLE 27

4-(1H-indol-4-yl)-1-(2-phenoxyethyl)-4-piperidinol

Using the procedure of Example 6, 8 g of the hydrochloride of Example 3, 100 ml of dimethylformamide, 10 g of sodium carbonate and 7.6 g of β-bromo-phenetol were reacted to obtain 10.2 g of product which was crystallized from isopropanol and then acetonitrile to obtain 4-(1H-indol-4-yl)-1-(2-phenoxyethyl)-4-piperidinol melting at 168° C.

EXAMPLE 28

4-[1-(2-phenoxyethyl)-1,2,3,6-tetrahydro-pyridin-4-yl-1H-indole

Using the procedure of Example 17, 7.7 g of the product of Example 27 were reacted and the crude product was chromatographed over silica gel. Elution was effected with a 6-3-1 cyclohexane-chloroform-ethyl acetate mixture and the product was crystallized from petroleum ether (b.p.=60°–80° C.) to obtain 5.52 g of 4-[1-(2-phenoxyethyl)-1,2,3,6-tetrahydro-pyridin-4-yl-1H-indole which after crystallization from isopropyl ether melted at 95° C.

EXAMPLE 29

1,3-dihydro-4-[1-(2-phenoxyethyl)-1,2,3,6-tetrahydro-4-pyridinyl]-2H-indol-2-one hydrochloride Using the procedure of Example 13, 3.4 g of the product of Example 28, 35 ml of acetic acid and 1.57 g of N-chloro-succinimide were reacted and the product was chromatographed over silica gel. Elution with a 6-3-1 cyclohexane-chloroform-triethylamine mixture yielded 3.6 g of the 3-chloro derivative. 3.6 g of the 3-chloro derivative were reacted as in Example 21 to obtain 2.9 g of crude product which was crystallized from a methanol-isopropanol mixture to obtain 1,3-dihydro-4-[1-(2-phenoxyethyl)-1,2,3,6-tetrahydro-4-pyridinyl]-2H-indol-2-one hydrochloride melting at 270° C.

EXAMPLE 30

1-[4-(4-fluorophenyl-4-oxobutyl)]4-(1H-indole-4-yl)-4-piperidinol

A mixture of 3 g of the hydrochloride of Example 3, 60 ml of methyl isobutyl ketone, 3.8 g of sodium carbonate and 2.4 ml of p-fluorobutyrophenone chloride was refluxed under nitrogen for 24 hours and was cooled. The mixture was washed with acetone and evaporated to dryness at 50° C. under reduced pressure. The residue was chromatagraphed over silica gel and eluted with a 6-3-1 chloroform-acetone-triethylamine mixture. The product was crystallized from ethyl acetate to obtain 3.2 g of 1-[4-(4-fluorophenyl-4-oxobutyl)]4-(1H-indole-4-yl)-4-piperidinol melting at 190° C.

Using the procedure of Example 5, a mixture of the 3.2 g of the free base, 300 ml of isopropanol and 1 g of fumaric acid was refluxed to obtain 3.7 g of the acid fumarate of the base melting at 223° C.

EXAMPLE 31

4-[1-[(4-fluorophenyl)-4-oxobutyl]-1,2,3,6-tetrahydro-4-pyridinyl]-1H-indole

Using the procedure of Example 11, 1.4 g of the product of Example 30, 20 ml of ethanol and 40 ml of N hydrochloric acid were reacted to obtain 0.95 g of 4-[1-[(4-fluorophenyl)-4-oxobutyl]-1,2,3,6-tetrahydro-4-pyridinyl]-1H-indole melting at 155° C.

EXAMPLE 32

1,3-dihydro-4-[1-[(4-fluorophenyl)-4-oxobutyl]-1,2,3,6-tetrahydro pyridin-4-yl]-2H-indole-2-one hydrochloride Using the procedure of Example 13, 0.95 g of the product of Example 31, 100 ml of acetic acid and 0.385 g of N-chloro succinimide were reacted to obtain 1 g of crude product which was chromatographed over silica gel and eluted with a 6-3-1 cyclohexane-chloroform-triethylamine mixture to obtain 0.9 g of the 3-chloro derivative. The latter was reacted as in Example 21 to obtain 0.74 g of crude product which was crystallized from a methanol-isopropanol mixture to obtain 0.65 g of 1,3-dihydro-4-[1-[(4-fluorophenyl)-4-oxobutyl]-1,2,3,6-tetrahydro pyridin-4-yl]-2H-indole-2-one hydrochloride melting at 254° C.

EXAMPLE 33

1-propionitrile-4-(1H-indol-4-yl)-4-piperidinol

A mixture of 2.95 g of the base of Example 3, 15 ml of acrylonitrile and a trace of monoethyl hydroquinone ether was cooled to 5° C. and stirred for one hour at 5° C. and was filtered. The product was rinsed with ether and then with isopropanol to obtain 2.26 g of 1-propionitrile-4-(1H-indol-4-yl)-4-piperidinol melting at 190°–191° C.

EXAMPLE 34

4-(1-propionitrile-1,2,3,6-tetrahydropyridin-4-yl)-1H-indole

Using the procedure of Example 17, 3.8 g of the product of Example 33 was refluxed for 5½ hours to obtain 2.26 g of 4-(1-propionitrile-1,2,3,6-tetrahydropyridin-4-yl)-1H-indole melting at 134°–135° C.

1.165 g of the base were partially dissolved in 30 ml of ethanol and after the addition of 538 mg of fumaric acid, 58 ml of ethanol and 29 ml of methanol thereto, the mixture was refluxed until complete dissolution occurred. The mixture was filtered hot, concentrated and cooled. After standing for 90 minutes at 4° C., the recovered product was rinsed with ethanol and dried at 100° C. under reduced pressure to obtain 0.872 g of the neutral fumarate of the base melting at 190°–191° C.

EXAMPLE 35

Also produced was 4-(1-allyl-1,2,3,6-tetrahydro-pyridin-4-yl)-1H-indole and its fumarate melting at 196° C.

EXAMPLE 36

An intra-muscular injectable solution was prepared from 20 mg of the product of Example 13 and sufficient sterile solvent for a total volume of 2 ml.

Tablets were prepared containing 20 mg of the product of Example 13 and sufficient excipient of lactose, starch, talc and magnesium stearate for a final weight of 350 mg.

PHARMACOLOGICAL STUDY (1) Bond to the opiate receptor μ in vitro

Membrane residues preserved at −30° C. for about 30 days and prepared from brains of rats were used in this test and these residues were suspended in Tris buffer pH 7.7. Fractions of 2 ml were distributed into hemolysis tubes and $^3$H dihydromorphine 0.7 nM and the product to be studied were added. The products were first of all tested with $5 \times 10^{-6}$M in triplicate. When the tested products displaced more than 50% of the radioactivity specifically linked to the receptor, they were tested again according to a range of 7 doses to determine the dose which inhibited by 50% the radioactivity specifically linked to the receptor. The 50% inhibiting concentration was thus determined.

The non-specific bond was determined by addition of $10^{-5}$M morphine in triplicate. After incubating at 25° C. for 40 minutes, returning to the water-bath at 0° C. for 5 minutes, filtering under vacuum, rinsing with Tris buffer pH 7.7, the radioactivity was counted in the presence of scintillating Trition. The results were expressed: either directly as 50% inhibiting concentration (IC$_{50}$), that is as a concentration of the product studied, expressed in nM, necessary to displace 50% of the specific radioactivity fixed on the receptor studied, or in relative bond affinity (RBA), taking morphine=100 as a reference $$RBA = \frac{IC_{50} \text{ morphine} \times 100}{IC_{50} \text{ of the product studied}}$$

The results are reported in the following Table

TABLE

| Compound of Example | IC50 | RBA |
|---|---|---|
| 11 | 9.43 | 22.43 |
| 13 | 1.4 | 270 |
| 14 | 28 | 13 |
| 26 | 59 | 8.2 |
| 29 | 11 | 23 |
| 32 | 3.5 | 62 |

(2) Bond to the opiate receptor K in vitro

Membrane residues prepared from guinea-pig cerebellum kept at −30° C. for about 30 days were used and these residues were suspended in Tris buffer pH 7.7. Fractions of 2 ml were distributed into hemolysis tubes, and 9$^3$H Ethylketocyclazocin 1 nM and the product to be studied were added. The products were first tested to $5 \times 10^{-6}$M in triplicate. When the products tested displaced more than 50% of the radioactivity specifically linked to the receptor, they were tested again according to a range of 7 doses to determine the dose which inhibited by 50% the radioactivity specifically linked to the receptor. In this way, the 50% inhibiting concentration was determined.

The non-specific bond was determined by the addition of a product known as U 50488 H(ref. Up. John) to $10^{-5}$M in triplicate. After incubating at 25° C. for 40 minutes, returning to the water-bath at 0° C. for 5 minutes, filtering under reduced pressure, and rinsing in Tris buffer pH 7.7, the radioactivity was counted in the presence of scintillating Trition. The results were expressed: either directly as 50% inhibiting concentration (IC$_{50}$), that is as a concentration of the product studied, expressed in nM, necessary to displace 50% of the specific radioactivity fixed on the receptor studied, or in relative bond affinity (=RBA) taking the product U 50 488 H as reference $$RBA = \frac{IC_{50} \times (U\ 50488\ H) \times 100}{IC_{50} \text{ of product studied}}$$

The results are reported in the following Table

| Product of Example | IC50 | RBA |
|---|---|---|
| 7 | 182 | 1.4 |
| 32 | 460 | 1.3 |
| 29 | 152 | 1.1 |

(3) Analgesic activity

Warm plate test

Female mice weighing from 22 to 24 g were placed one by one on a copper plate maintained at 56° C. The reaction to pain was shown by the animals licking their front paws and the time of this reaction was noted and was only retained when the mice reacted in less than 8 seconds. The animals were divided into equal groups and were treated with the products to be studied, one group receiving only the vehicle. The time of reaction to pain was again measured 30 to 60 minutes after the treatment and the active dose or AD$_{100}$ was the dose which increased the reaction time by 100%, 60 minutes after the treatment, taking account of the variations of the reaction time of the control animals.

| Compound of Example | AD100 |
|---|---|
| 14 | 0.5 mg/kg intracerebral ventricle route |
| 13 | 20 mg/kg oral route |

The analgesic activity of these products was antagonized by naloxone.

BIBLIOGRAPHY

Eddy, et al "Synthetic analgesics, Vol. II Diethienylbutenyl and diethienylbutylamine." J. Pharmacol. Exp. Thev., (1953), Vol. 107, 385.

Various modifications of the compounds and method of the invention may be made without departing from the spirit or scope thereof and it is to be understood that the invention is intended to be limited only as defined in the appended claims.

What we claim is:

1. A compound selected from the group consisting of an indole of the formula

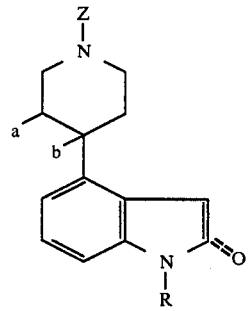

wherein R is selected from the group consisting of hydrogen, alkyl of 1 to 8 carbon atoms and aralkyl of 7 to 12 carbon atoms, Z is selected from the group consisting of hydrogen, alkyl of 1 to 8 carbon atoms, alkenyl of 2 to 8 carbon atoms, cyanoalkyl of 3 to 8 carbon atoms, hydrdoxyalkyl of 2 to 8 carbon atoms, —(CH$_2$)$_n$—O—B,

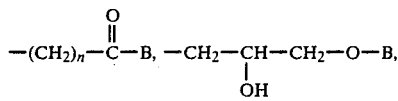

aralkyl of 7 to 12 carbon atoms optionally substituted with a member of the group consisting of alkyl and alkoxy of 1 to 5 carbon atoms, halogen, —OH, CF$_3$—, CF$_3$O—, —NH$_2$ and —NO$_2$ and cycloalkylalkyl of 4 to 12 carbon atoms, n is one integer from 2 to 8, B is selected from the group consisting of phenyl, naphthyl, pyridyl, thienyl and thiazolyl, all optionally substituted with a member of the group consisting of alkyl and alkoxy of 1 to 5 carbon atoms, halogen, —OH, hydroxyalkyl of 1 to 5 carbon atoms, nitro, amino, CF$_3$—, alkenyl and alkenyloxy of 2 to 5 carbon atoms and alknyl and alkylnyloxy of 2 to 5 carbon atoms, a and b are both hydrogen or a is hydrogen and b is —OH or alkoxy of 1 to 8 carbon atoms or a and b together form a carbon-carbon bond and the 2-oxo with dotted lines indicates its optional presence when the double bond in the indole ring is missing and a non-toxic, pharmaceutically acceptable acid addition salt.

2. A compound of claim 1 wherein R is alkyl of 1 to 4 carbon atoms or hydrogen.

3. A compound of claim 1 wherein Z is selected from the group consisting of hydrogen, alkyl of 1 to 4 carbon atoms, —(CH$_2$)$_n$—O—B and

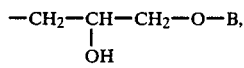

n is an integer from 2 to 4 and B is optionally substituted phenyl or thienyl.

4. A compound of claim 1 wherein Z is

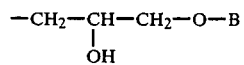

and B is phenyl substituted with propenyloxy.

5. A compound of the claim 1 wherein a and b are both hydrogen.

6. A compound of claim 1 wherein a and b together form a carbon-carbon bond.

7. A compound of claim 1 wherein a is hydrogen and b is —OH or methoxy.

8. A compound of claim 1 selected from the group consisting of 1,3-dihydro-4-[1-(2-hydroxy-3-[2-(2-propenyloxy)-phenoxy]-propyl)-1,2,3,6-tetrahydro-4-pyridinyl]-2H-indole-2-one and its hydrochloride, 4-(4-methoxy-4-piperidinyl)-1H-indole and its fumarate and 4-(1H-indole-4- yl)α-[[2-(2-propenyloxy)-phenoxy]-methyl]-1,2,3,6-tetrahydro-1-pyridine-ethanol and its oxalate.

9. An analgesic composition comprising an analgesically effective amount of at least one compound of claim 1 and a pharmaceutical carrier.

10. A composition of claim 9 wherein in the compound, R is alkyl of 1 to 4 carbon atoms or hydrogen.

11. A composition of claim 9 wherein in the compound, Z is selected from the group consisting of hydrogen, alkyl of 1 to 4 carbon atoms, —(CH$_2$)$_n$—O—B and

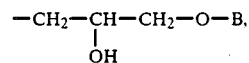

n is an integer from 2 to 4 and B is optionally subsyituted phenyl or thienyl.

12. A composition of claim 9 wherein in the compound, Z is

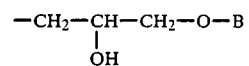

and B is phenyl substituted with propenyloxy.

13. A composition of claim 9 wherein in the compound, a and b are both hydrogen.

14. A composition of claim 9 wherein in the compound, a and b together form a carbon-carbon bond.

15. A composition of claim 9 wherein in the compound, a is hydrogen and b is —OH or methoxy.

16. A composition of claim 9 wherein the active compound is selected from the group consisting of 1,3-dihydro-4-[1-(2-hydroxy-3-[2-(2-propenyloxy)-phenoxy]-propyl)-1,2,3,6-tetrahydro-4-pyridinyl]-2H-indole-2-one and its hydrochloride, 4-(4-methoxy-4-piperidinyl)-1H-indole and its fumarate and 4-(1H-indole 4-yl)α- [[2-(2-propenyloxy)-phenoxy]-methyl]-1,2,3,6-tetrahydro-1-pyridine-ethanol and its oxalate.

17. A method of relieving pain in warm-blooded animals comprising administering to warm-blooded animals an analgesically effective amount of a compound of claim 1.

18. A method of claim 17 wherein in the oompound R is alkyl of 1 to 4 carbon atoms or hydrogen.

19. A method of claim 17 wherein in the compound, Z is selected from the group consisting of hydrogen, alkyl of 1 to 4 carbon atoms, —(CH$_2$)$_n$—O—B and

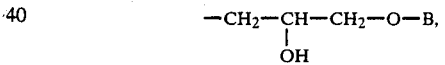

n is an integer from 2 to 4 and B is optionally substituted phenyl or thienyl.

20. A method of claim 17 wherein in the compound, Z is

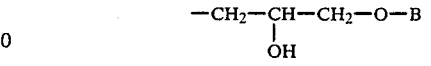

and B is phenyl substituted with propenyloxy.

21. A method of claim 17 wherein in the compound, a and b are both hydrogen.

22. A method of claim 17 wherein in the compound, a and b form together a carbon-carbon bond.

23. A method of claim 17 wherein in the compound, a is hydrogen and b is —OH or methoxy.

24. A method of claim 17 wherein the active compound is selected from the group consisting of 1,3-dihydro-4-[1-(2-hydroxy-3-[2-(2-propenyloxy)-phenoxy]-propyl)-1,2,3,6-tetrahydro-4-pyridinyl]-2H-indole-2-one and its hydrochloride, 4-(4-methoxy-4-piperidinyl)-1H-indole and its fumarate and 4-(1H-indole-4 yl)α-[[2-(2-propenyloxy)-phenoxy]-methyl]-1,2,3,6-tetrahydro-1-pyridine-ethanol and its oxalate.

* * * * *